(12) United States Patent
Tachibana et al.

(10) Patent No.: US 7,820,003 B2
(45) Date of Patent: Oct. 26, 2010

(54) METHOD FOR PRODUCING DIAPER

(75) Inventors: Ikuo Tachibana, Osaka (JP); Toyoshi Umebayashi, Osaka (JP)

(73) Assignee: Zuiko Corporation, Osaka (JP)

( * ) Notice: Subject to any disclaimer, the term of this patent is extended or adjusted under 35 U.S.C. 154(b) by 237 days.

(21) Appl. No.: 11/916,481

(22) PCT Filed: Jul. 4, 2006

(86) PCT No.: PCT/JP2006/313294
§ 371 (c)(1),
(2), (4) Date: Dec. 4, 2007

(87) PCT Pub. No.: WO2007/004640
PCT Pub. Date: Jan. 11, 2007

(65) Prior Publication Data
US 2009/0126864 A1    May 21, 2009

(30) Foreign Application Priority Data
Jul. 5, 2005    (JP)    ................ 2005-196281

(51) Int. Cl.
*A61F 13/15* (2006.01)
(52) U.S. Cl. ....................... 156/204; 156/216
(58) Field of Classification Search .......... 156/204, 156/226, 227
See application file for complete search history.

(56) References Cited
U.S. PATENT DOCUMENTS 6,582,543 B1 * 6/2003 Nilsson et al. ............... 156/216
6,936,129 B2 * 8/2005 Karami et al. ............... 156/265
2002/0193776 A1   12/2002 Fernfors
2006/0244166 A1   11/2006 Wada et al.

FOREIGN PATENT DOCUMENTS

| JP | 2003-93443 | 4/2003 |
|----|------------|--------|
| JP | 2004-508138 | 3/2004 |
| JP | 2004-516072 | 6/2004 |
| WO | 02/22062 | 3/2002 |
| WO | 02/49568 | 6/2002 |
| WO | 2004/054490 | 7/2004 |

OTHER PUBLICATIONS

International Search Report for corresponding Application No. PCT/JP2006/313294 dated Oct. 3, 2007.

* cited by examiner

*Primary Examiner*—Richard Crispino
*Assistant Examiner*—B. Musser
(74) *Attorney, Agent, or Firm*—Renner, Otto, Boisselle & Sklar, LLP

(57) ABSTRACT

A method for producing a diaper of the present invention includes the steps of: folding back a first strip-shaped portion 13 and a second strip-shaped portion 23; successively forming pairs of first and second belts 1 and 2 by cutting first and second separate webs W1 and W2; placing pairs of the first and second belts 1 and 2 at a predetermined interval P in a carrying direction Y of a continuous piece; temporarily attaching the first and second belts 1 and 2 to a portion of the continuous piece to be a back portion; fixing the belts 1 and 2 to the continuous piece; and severing the continuous piece with the belts 1 and 2 fixed thereon at a predetermined pitch into individual diapers.

1 Claim, 14 Drawing Sheets

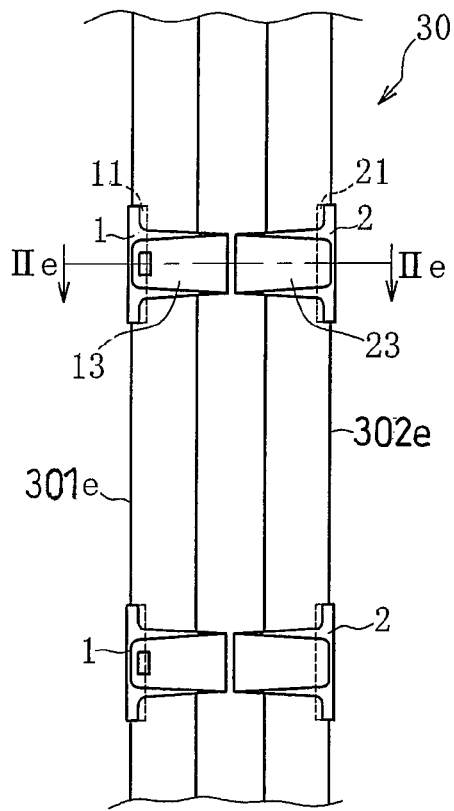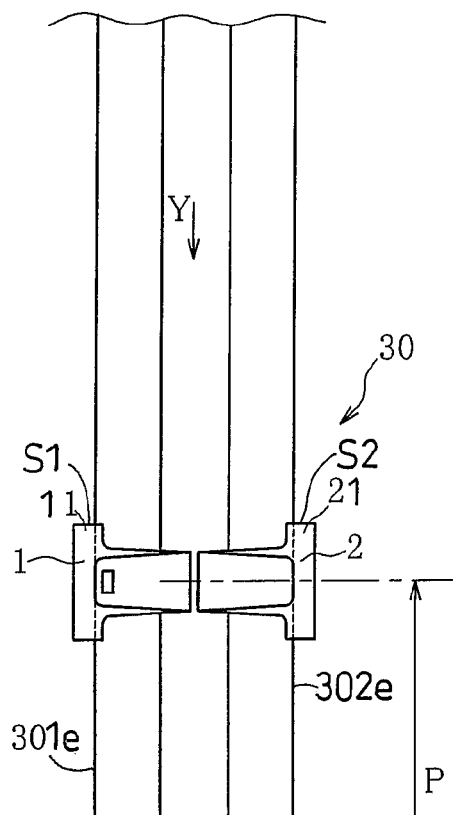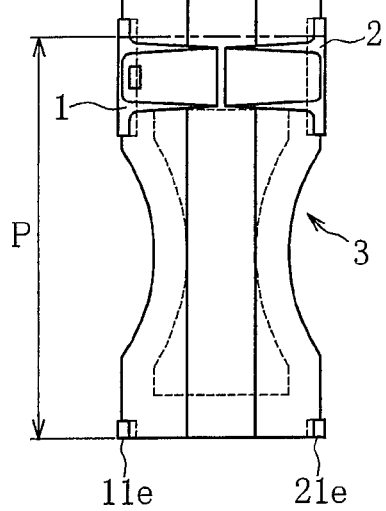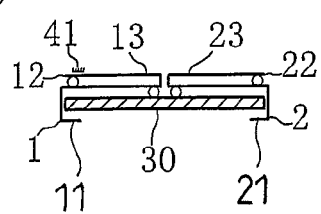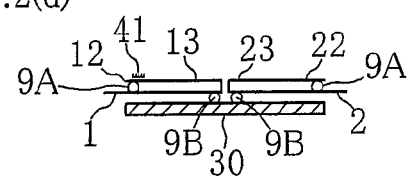

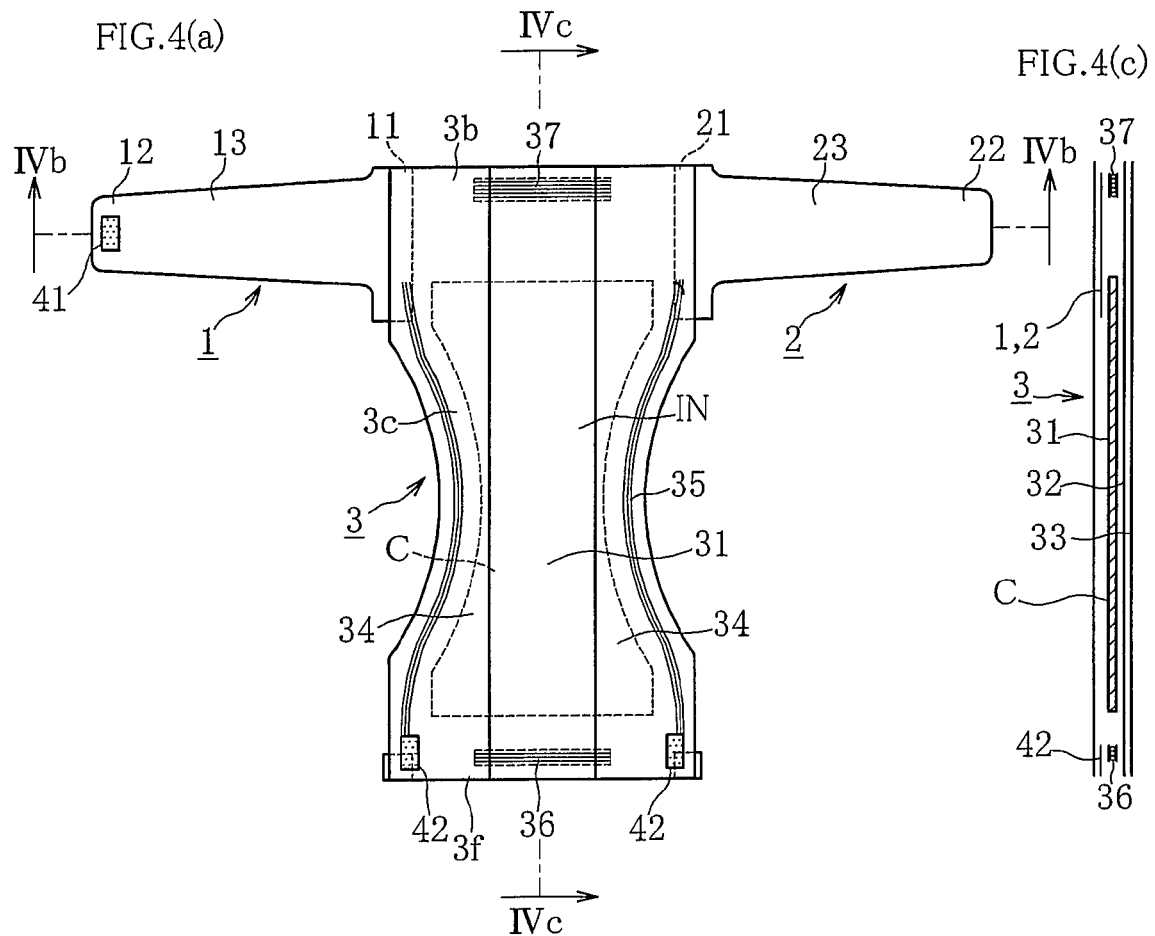
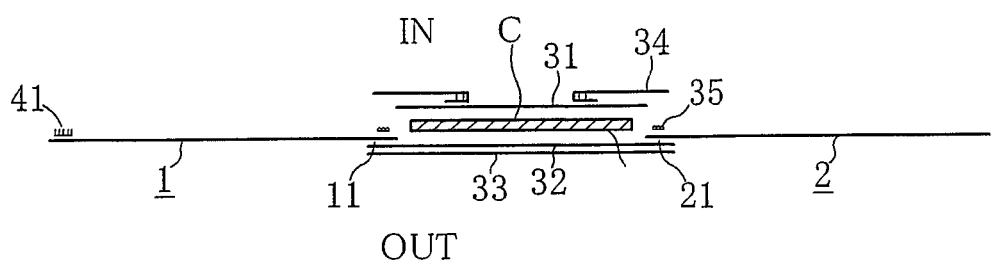

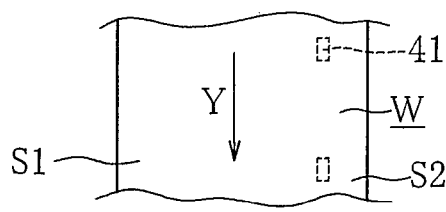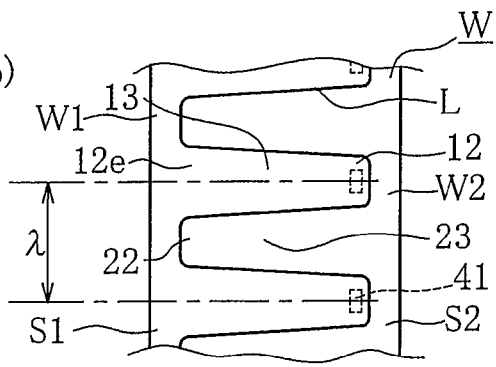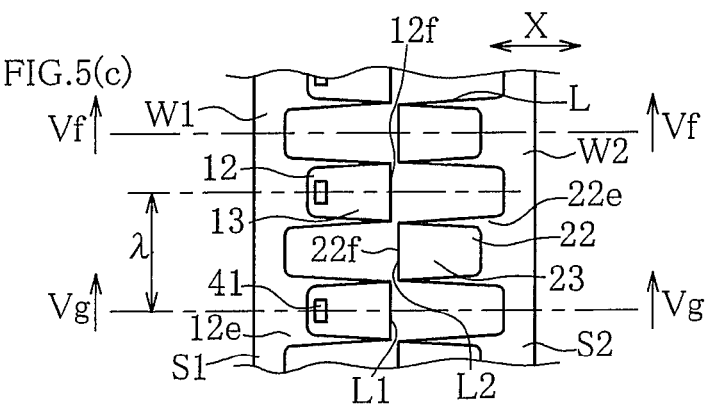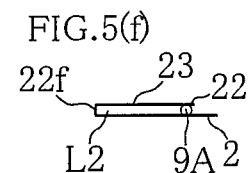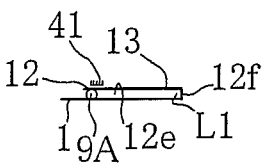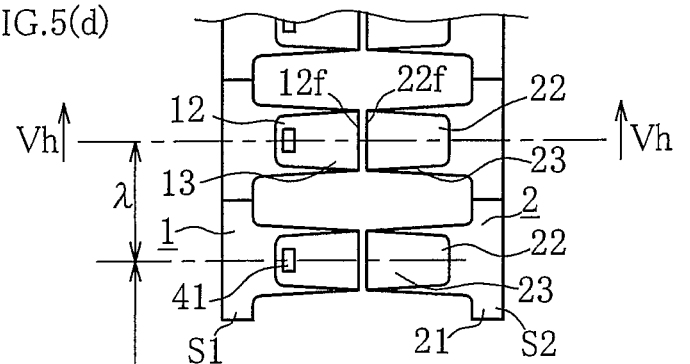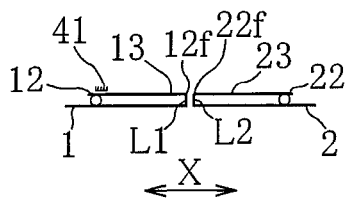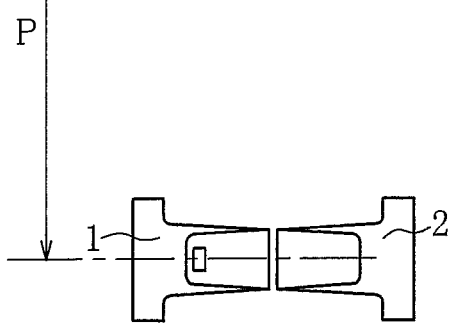

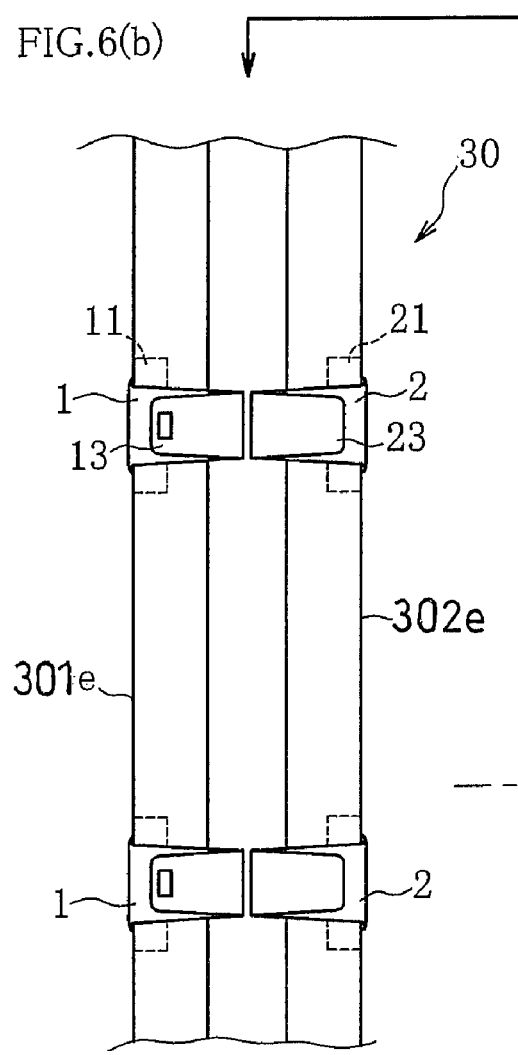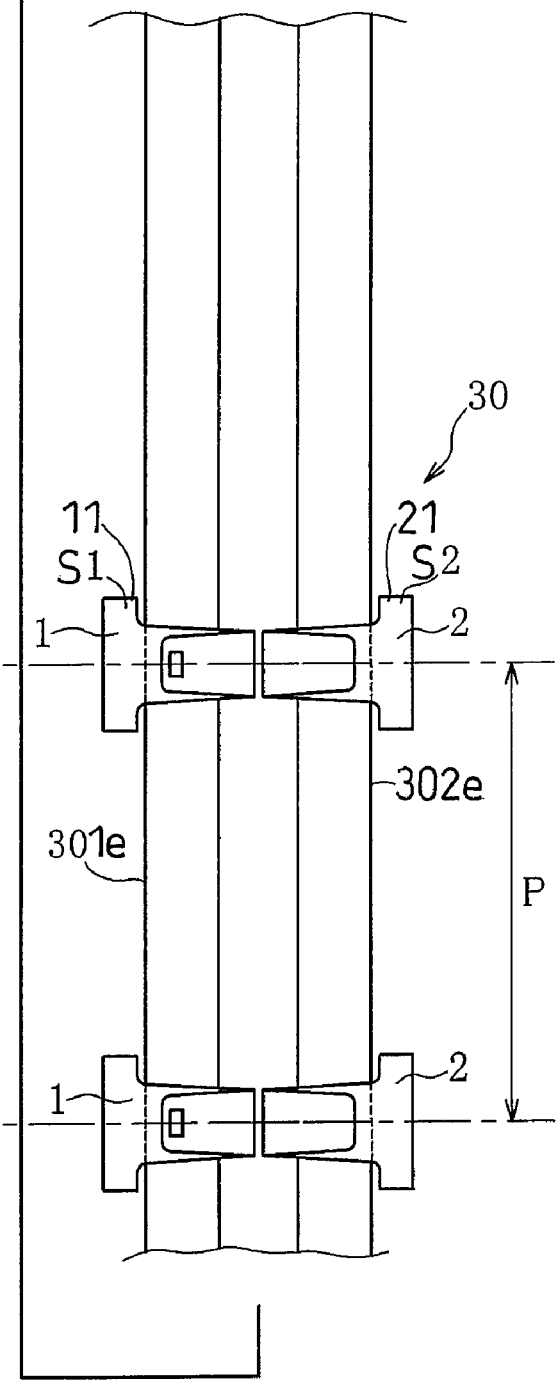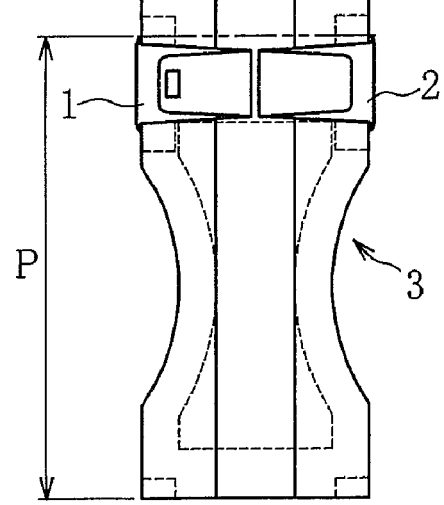

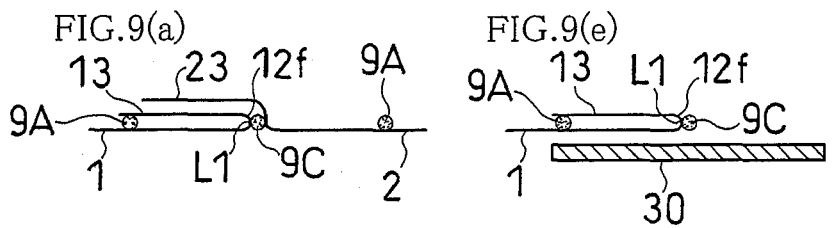
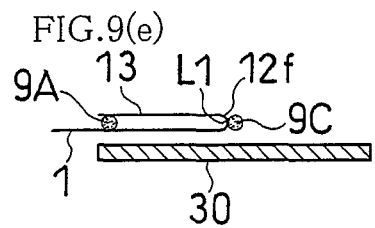
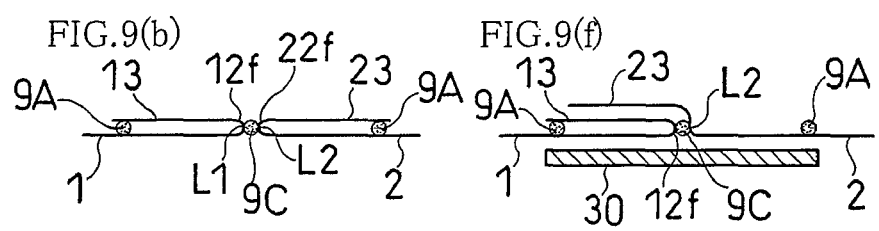
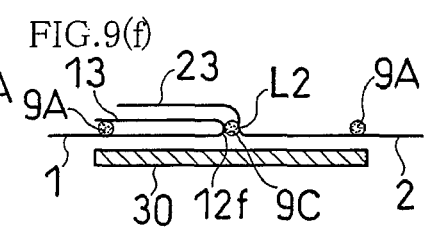
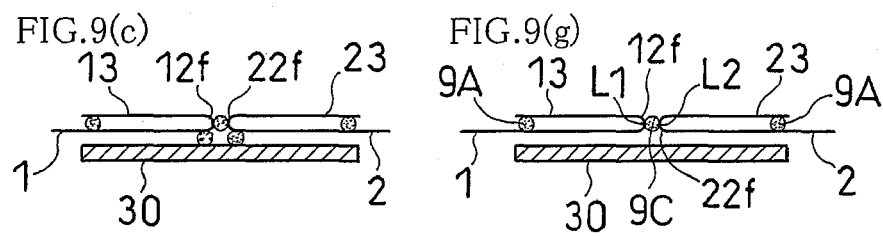
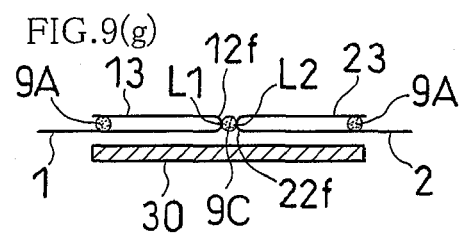
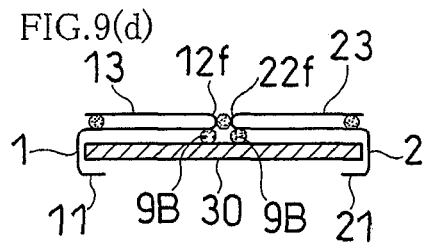
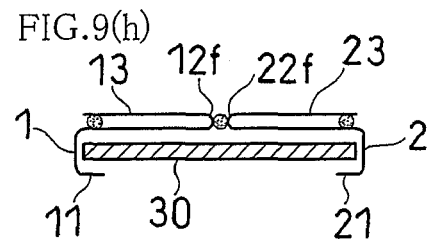
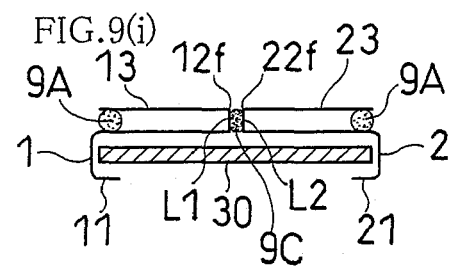

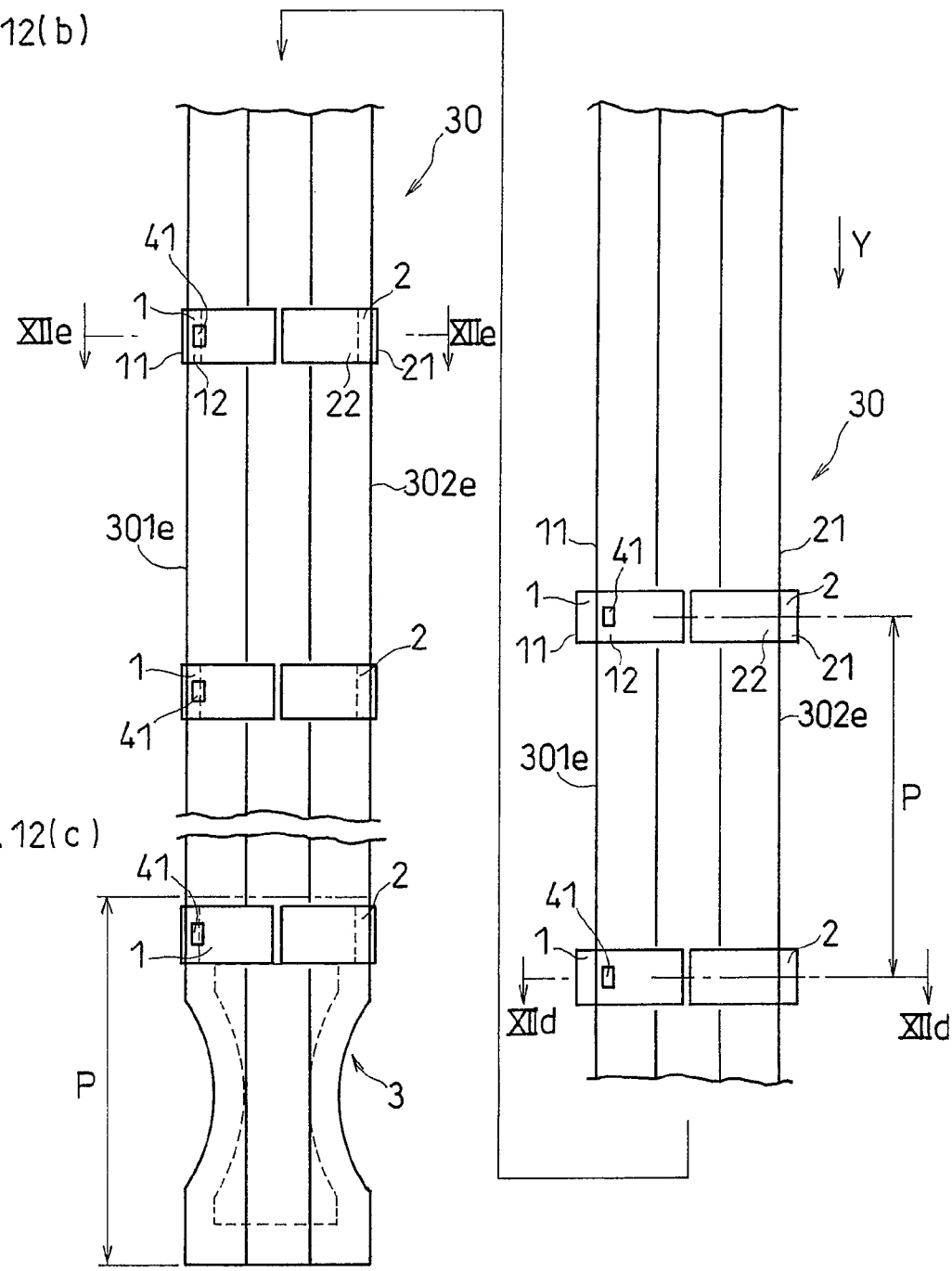

METHOD FOR PRODUCING DIAPER

TECHNICAL FIELD

The present invention relates to a method for producing a diaper with belts.

BACKGROUND ART

A diaper with belts is suitable for being worn by the wearer themselves while the wearer is in a stand-up position. Diapers of this type include those disclosed in the following three patent documents.

First Patent Document: Japanese Laid-Open Patent Publication No. 2003-93443 (ABSTRACT)

Second Patent Document: Japanese National Phase PCT Laid-Open Publication No. 2004-508138 (WO2002/022062) (ABSTRACT)

Third Patent Document: Japanese National Phase PCT Laid-Open Publication No. 2004-516072 (WO2002/049568) (ABSTRACT)

DISCLOSURE OF THE INVENTION

For a diaper with belts, it is important to prevent positional displacements between two belts. Typically, an apparatus for cutting and placing two long belts of a diaper is likely to have a complicated structure.

Therefore, an object of the present invention is to provide a method for producing a diaper, which is capable of producing a diaper in which positional displacements between belts are unlikely to occur, and for which the apparatus has a simple structure.

In diapers disclosed in the patent documents above, the belt has a constant width. In order to fit the back portion of a diaper to the back side (back part) of the wearer, it is preferred to increase the width of the belt. However, a belt with a broad width may deteriorate the wearability in the abdominal part of the wearer.

If one employs a belt with a larger width on the back side of the wearer and a smaller width in the abdominal part of the wearer, the belt shape will be tapered, thus resulting in a waste of the belt material.

Therefore, another object of the present invention is to provide a method for producing a diaper, which is capable of producing a diaper whose back portion easily fits to the back side of the wearer, which has desirable wearability around the abdominal part of the wearer, and which wastes none of the belt material. Still another object of the present invention is to improve the feel (or the appearance) of a diaper.

A method for producing a diaper according to the first invention is a method for producing a diaper, the diaper including: a diaper main body including a front portion covering an abdominal side of a wearer, a back portion covering a back side of the wearer, and a crotch portion between the front portion and the back portion; a first belt including a first end portion fixed to one end portion of the back portion in an around-the-torso direction; and a second belt including a second end portion fixed to the other end portion of the back portion in the around-the-torso direction, wherein the first and second belts are attached to each other when wearing the diaper to thereby fasten the diaper around the torso of the wearer, the method including the steps of: carrying a strip-shaped first web being continuous in a carrying direction and including a first lateral portion to be the first end portion; folding back the first web along a first folding line that is continuous in a longitudinal direction of the first web while carrying the first web; carrying a strip-shaped second web being continuous in a carrying direction and including a second lateral portion to be the second end portion; folding back the second web along a second folding line that is continuous in a longitudinal direction of the second web while carrying the second web; changing a carrying path of the first web and/or that of the second web so that the first folding line and the second folding line come close to each other or coincide with each other; successively forming pairs of the first and second belts by cutting the first web and the second web along cut-off lines extending in the width direction of the webs after the step of folding back the first and second webs and the step of changing the carrying path; placing pairs of the first and second belts at a predetermined interval in a carrying direction of a continuous piece forming the diaper main body so that each pair is laid on a portion of the continuous piece to be the back portion; temporarily attaching the first and second belts, which have been placed at the predetermined interval, to the portion of the continuous piece to be the back portion; fixing each pair of the first and second belts to the continuous piece by fixing the first lateral portion of the first belt to a portion of the continuous piece to be one end portion of the back portion in the around-the-torso direction and fixing the second lateral portion of the second belt to a portion of the continuous piece to be the other end portion of the back portion in the around-the-torso direction; and severing the continuous piece with the first and second belts fixed thereon at the predetermined interval into individual diapers.

According to the first invention, the cutting process and the placement process are performed after the folded first and second webs are brought closer to each other, and therefore the cutting process and the placement process can be performed for each pair of belts, whereby there is unlikely a positional displacement between belts. This also simplifies the structure of the apparatus.

In a preferred embodiment of the first invention, in the step of folding back the first web, the first web is folded back so that the first lateral portion is not laid on portions of the first web other than the first lateral portion; in the step of folding back the second web, the second web is folded back so that the second lateral portion is not laid on portions of the second web other than the second lateral portion; in the step of placing pairs of the first and second belts, the pairs of the first and second belts are placed so that the first lateral portion protrudes from a first side edge of the continuous piece and the second lateral portion protrudes from a second side edge of the continuous piece opposing the first side edge; and in the step of fixing each pair of belts to the continuous piece, at least a portion of the first lateral portion protruding from the first side edge of the continuous piece is folded back so that the continuous piece is sandwiched between the first lateral portion and another portion of the first belt other than the first lateral portion, after which the folded portion of the first lateral portion is at least partially fixed to a portion of the continuous piece in a vicinity of the first side edge, and at least a portion of the second lateral portion protruding from the second side edge of the continuous piece is folded back so that the continuous piece is sandwiched between the second lateral portion and another portion of the second belt other than the second lateral portion, after which the folded portion of the second lateral portion is at least partially fixed to a portion of the continuous piece in a vicinity of the second side edge.

In the first invention, if the belts are attached and fixed to the back portion without being folded back, the attachment between the belts and the back portion can be easily peeled off when the belts are pulled when wearing the diaper. In contrast, if the belts are folded back and the folded portions of the belts are attached and fixed to the back portion as in this embodiment, the attachment between the belts and the back portion is unlikely to be peeled off even if the belts are pulled when wearing the diaper.

Moreover, when wearing the diaper, the free ends of the belts can be easily peeled off because non-overlapping lateral portions are folded back onto the back portion.

In another preferred embodiment of the first invention, the method further includes, after the step of changing the carrying path and before the step of cutting the first and second webs, a step of temporarily attaching a portion of the first web along the first folding line and a portion of the second web along the second folding line to each other to form a single temporarily-attached web.

In this embodiment, two webs are temporarily attached to each other, which can therefore be handled as a single web in subsequent steps, thus simplifying the production facilities.

A method for producing a diaper according to the second invention is a method for producing a diaper, the diaper including: a diaper main body including a front portion covering an abdominal side of a wearer, a back portion covering a back side of the wearer, and a crotch portion between the front portion and the back portion; a first belt including a first end portion fixed to one end portion of the back portion in an around-the-torso direction; and a second belt including a second end portion fixed to the other end portion of the back portion in the around-the-torso direction, wherein the first and second belts are attached to each other when wearing the diaper to thereby fasten the diaper around the torso of the wearer, the method including the steps of: carrying a strip-shaped web being continuous in a carrying direction and including a first lateral portion to be the first end portion and a second lateral portion to be the second end portion; cutting the web along a wave-shaped cut-off line that is continuous in a longitudinal direction of the web while carrying the web to thereby form a comb-shaped first separate web and a comb-shaped second separate web, the comb-shaped first separate web including a plurality of first strip-shaped portions extending in the width direction of the web, with the first strip-shaped portions being connected together along the first lateral portion of the web, and the comb-shaped second separate web including a plurality of second strip-shaped portions extending in the width direction of the web, with the second strip-shaped portions being connected together along the second lateral portion of the web; folding back the first strip-shaped portion along a first folding line that extends in a longitudinal direction of the web so that one portion and another portion of the first strip-shaped portion are laid on each other and temporarily attaching the one portion and the other portion of the first strip-shaped portion to each other; folding back the second strip-shaped portion along a second folding line that extends in a longitudinal direction of the web so that one portion and another portion of the second strip-shaped portion are laid on each other and temporarily attaching the one portion and the other portion of the second strip-shaped portion to each other; successively forming pairs of the first belt including the first strip-shaped portion and the second belt including the second strip-shaped portion by cutting the first separate web in the first lateral portion and cutting the second separate web in the second lateral portion; placing pairs of the first and second belts at a predetermined interval in the carrying direction of a continuous piece forming the diaper main body so that each pair is laid on a portion of the continuous piece to be the back portion; temporarily attaching the first and second belts, which have been placed at the predetermined interval, to the portion of the continuous piece to be the back portion; fixing each pair of the first and second belts to the continuous piece by fixing the first lateral portion of the first belt to a portion of the continuous piece to be the one end portion of the back portion in the around-the-torso direction and fixing the second lateral portion of the second belt to a portion of the continuous piece to be the other end portion of the back portion in the around-the-torso direction; and severing the continuous piece with the first and second belts fixed thereon at the predetermined interval into individual diapers.

With a diaper produced by the method of the second invention, the width of each belt is decreasing toward the tip of the belt, whereby the belts will not be obstructive around the abdominal part of the wearer, thus improving the wearability.

The belts have an increased width on the back side of the wearer, whereby the entire back portion of the diaper is likely to fit to the back side of the wearer.

Since the strip-shaped belts are produced by cutting the web, the material is not wasted and the product has a desirable appearance.

In the present invention, the term "temporary attachment" refers to attaching belts and other members in such a manner that it is possible to easily peel a belt and other members off the other belt or off the diaper main body without substantially damaging the belts or the diaper main body. Typically, a "temporarily attached" portion can more easily be peeled off than a "fixed" portion.

In the present invention, the term "diaper" includes worn articles capable of absorbing urine, feces, etc., and also includes worn articles of which the primary purpose is to absorb small amounts of urine such as incontinence pads.

In a preferred embodiment of the second invention, in the step of placing pairs of the first and second belts, the pairs of the first and second belts are placed so that the first lateral portion protrudes from a first side edge of the continuous piece and the second lateral portion protrudes from a second side edge of the continuous piece opposing the first side edge; and in the step of fixing each pair of belts to the continuous piece, at least a portion of the first lateral portion protruding from the first side edge of the continuous piece is folded back so that the continuous piece is sandwiched between the first lateral portion and the first strip-shaped portion, after which the folded portion of the first lateral portion is at least partially fixed to a portion of the continuous piece in a vicinity of the first side edge, and at least a portion of the second lateral portion protruding from the second side edge of the continuous piece is folded back so that the continuous piece is sandwiched between the second lateral portion and the second strip-shaped portion, after which the folded portion of the second lateral portion is at least partially fixed to a portion of the continuous piece in a vicinity of the second side edge.

In the second invention, as the belts are folded back and the folded portions of the belts are attached and fixed to the back portion, the attachment between the belts and the back portion is unlikely to be peeled off even if the belts are pulled when wearing the diaper.

In another preferred embodiment of the second invention, the method further includes a step of relatively displacing the first separate web and second separate web in such a direction that the first lateral portion and the second lateral portion move away from each other; in the step of placing pairs of the first and second belts, the pairs of the first and second belts are placed so that generally an entire portion of the first lateral portion of the first belt protrudes from the first side edge of the continuous piece and generally an entire portion of the second lateral portion of the second belt protrudes from the second side edge of the continuous piece; and in the step of fixing each pair of belts to the continuous piece, at least a portion of the first lateral portion protruding from the first side edge of the continuous piece is folded back so that the continuous piece is sandwiched between the first lateral portion and the first strip-shaped portion, after which the folded portion of the first lateral portion is at least partially fixed to a portion of the continuous piece in a vicinity of the first side edge, and at least a portion of the second lateral portion protruding from the second side edge of the continuous piece is folded back so that the continuous piece is sandwiched between the second lateral portion and the second strip-shaped portion, after which the folded portion of the second lateral portion is at least partially fixed to a portion of the continuous piece in a vicinity of the second side edge.

In this embodiment, the first lateral portion can be made to substantially protrude from the continuous piece through the displacement step. Therefore, as the first lateral portion is folded back, generally an entire portion of the first lateral portion of an increased width is laid on the back portion, and the first lateral portion of an increased width does not protrude from the diaper main body, thus improving the appearance. Moreover, the belts can be more strongly fixed to the back portion.

BRIEF DESCRIPTION OF THE DRAWINGS

FIGS. 2(a) to 2(c) are front views and FIGS. 2(d) and 2(e) are cross-sectional views taken along lines IId-IId and IIe-IIe, respectively, showing an example of a method for producing a diaper according to the present invention.

FIGS. 4(a), 4(b) and 4(c) are a front view, a cross-sectional view taken along line IVb-IVb and a cross-sectional view taken along line IVc-IVc, respectively, showing a diaper with belts being spread out.

FIGS. 5(a) to 5(e) are front views and FIGS. 5(f), 5(g) and 5(h) are cross-sectional views taken along lines Vf-Vf, Vg-Vg and Vh-Vh, respectively, showing an example of a method for producing belts according to the present invention.

FIGS. 6(a) to 6(c) are front views showing an example of a method for producing a diaper according to the present invention.

FIGS. 9(a) to 9(i) are schematic cross-sectional views showing a variation of the present invention.

FIGS. 12(a) to 12(c) are front views and FIGS. 12(d) and 12(e) are cross-sectional views taken along lines XIId-XIId and XIIe-XIIe, respectively, showing an example of a method for producing a diaper according to the present invention.

FIGS. 13(a), 3(b) and 3(c) are a back side view, a front view and a cross-sectional view taken along line XIIIc-XIIIc, respectively, showing a produced diaper.

DESCRIPTION OF THE REFERENCE NUMERALS

Figure 1A:
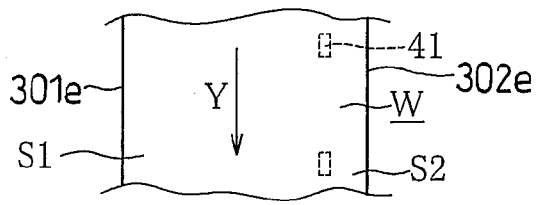
FIGS. 1(a) to 1(e) are front views and FIGS. 1(f), 1(g) and 1(h) are cross-sectional views taken along lines If-If, Ig-Ig and Ih-Ih, respectively, showing an example of a method for producing belts according to the present invention.

1: First belt
11: First end portion (fixed end portion)
13: First tapered portion (first strip-shaped portion)
2: Second belt
21: First end portion (fixed end portion)
23: Second tapered portion (second strip-shaped portion)
3: Diaper main body
3b: Back portion
3c: Crotch portion
3f: Front portion
41: First attachment member
42: Second attachment member
L: Cut-off line
L1: First folding line
L2: Second folding line
W: Web
W1: First separate web, first web
W2: Second separate web, second web
S1: First lateral portion
S2: Second lateral portion

BEST MODE FOR CARRYING OUT THE INVENTION

The present invention will be more clearly understood from the following description of preferred embodiments of the present invention taken in conjunction with the accompanying drawings. However, these embodiments and drawings are merely illustrative but should not be relied upon for defining the scope of the present invention, which is defined only by the appended claims. Like reference numerals denote like members throughout various figures.

First Embodiment

Embodiments of the present invention will now be described with reference to the drawings.

Before describing the production method thereof, an example of a diaper that can be produced by the present invention will first be described with reference to FIGS. 3(a) to 3(d) and 4(a) to 4(c).

Referring to FIG. 4(a), the diaper includes a diaper main body 3, a first belt 1 and a second belt 2. The diaper main body 3 includes a front portion 3f covering the abdominal side of the wearer, a back portion 3b covering the back side of the wearer, and a crotch portion 3c between the front portion 3f and the back portion 3b. The first and second belts 1 and 2 are provided so as to protrude oppositely in the around-the-torso direction from the back portion 3b. The belts 1 and 2 are provided so as to be attached to each other to thereby fasten the diaper around the torso of the wearer, as will be described later.

FIG. 4(c) is a cross-sectional view taken along line IVc-IVc in FIG. 4(a).

As shown in FIGS. 4(a) and 4(c), the diaper main body 3 includes a plurality of sheet-like members, an absorbent body and elastic members layered together.

As shown in FIGS. 4(a) and 4(c), the diaper main body 3 includes a liquid-permeable top sheet 31, an absorbent body C, a liquid-impermeable back sheet 32, and an outer sheet 33 layered together. Anti-leak walls (cuffs) 34 may be provided on the top sheet 31.

The absorbent body C may include a fluff pulp obtained by milling a pulp and/or a super absorbing polymer. The absorbent body C may be an air-laid pulp, or the like.

The anti-leak walls 34 prevent the feces and/or urine from leaking to the outside of the absorbent body C or the diaper. The anti-leak walls 34 may have a three-dimensional configuration. The diaper main body 3 may be provided with a plurality of elastic members 35 for preventing the feces and/or urine from leaking out of the diaper.

Elastic members 36 and 37 may be placed on the front portion 3f and the back portion 3b so as to form waist gathers for suppressing the slippage between the wearer and the diaper. The elastic members 35 to 37 may be rubber threads or rubber tapes.

First and second end portions (fixed end portions) 11 and 21 of the first and second belts 1 and 2 are fixed to end portions of the back portion 3b of the diaper main body 3 that are opposing each other in the around-the-torso direction. The first and second end portions 11 and 21 of the belts 1 and 2 are fixed while being sandwiched between the web forming the anti-leak walls 34 and the back sheet 32, for example.

The first belt 1 includes a first tapered portion (an example of the first strip-shaped portion) 13 which has an increased width at the first end portion 11 with the width gradually decreasing from the first end portion 11 toward a free end portion 12. The second belt 2 includes a second tapered portion (an example of the second strip-shaped portion) 23 which has an increased width at the second end portion 21 with the width gradually decreasing from the second end portion 21 toward a free end portion 22.

The tapered portions 13 and 23 do not always have to be formed in a smoothly tapered shape, but may alternatively have a strip shape whose width decreases stepwise toward the tip thereof. Alternatively, the strip-shaped portion may have a constant width, instead of being in a tapered shape.

A first attachment member 41 is fixed on the inner-surface side of the free end portion 12 of the first belt. The first attachment member 41 is detachably (so that it can later be detached) attached to the outer-surface side of the second belt 2. When the diaper is worn as shown in FIG. 3(d), the first attachment member 41 is attached to the central portion 23 or the free end portion 22 of the second belt 2. Thus, the first and second belts 1 and 2 and the back portion 3b are connected together into an annular shape so that the diaper fits to the torso part of the wearer. The wearer can adjust the fit by adjusting the position at which the first attachment member 41 is attached to the second belt 2 so as to conform to the torso of the wearer.

A second attachment member 42 is fixed on the inner-surface side of the front portion 3f of the diaper main body 3 of FIG. 4(a). As shown in FIG. 3(d), with the second attachment member 42, the front portion 3f is attached to the outer-surface side of the first and second belts 1 and 2 when the diaper is worn. Thus, the diaper can be placed over the crotch.

The term "inner-surface side" as used herein refers to the side to be in contact with the skin when the diaper is worn, and the term "outer-surface side" refers to the side which is opposite to the inner-surface side and to be exposed to the outside when the diaper is worn.

Touch fasteners or adhesive tapes may be employed, for example, as the attachment members 41 and 42 of FIG. 4(a). In the present embodiment, the material forming the anti-leak walls 34 and the first and second belts 1 and 2 is non-woven fabric, and the attachment members 41 and 42 are male touch fasteners, which are engaged with and attached to the surface of the non-woven fabric.

Female touch fasteners to be engaged with the male touch fasteners may be provided on the belts 1 and 2.

Next, an example of a method for producing a diaper will be described.

First, a method for producing pairs of the belts 1 and 2 will be described with reference to FIGS. 1 and 2.

Figure 1B:
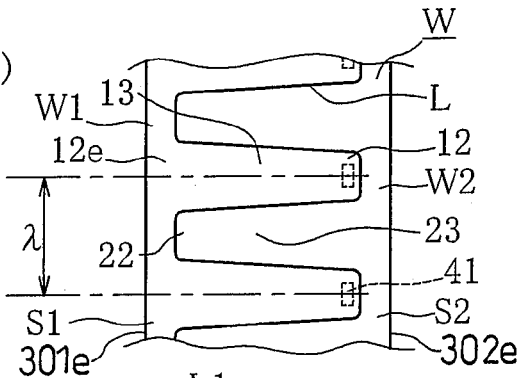

As shown in FIG. 1(a), while a strip-shaped continuous web W is carried in the direction of the arrow (the carrying direction) Y, a plurality of the first attachment members 41 are fixed to the web W at a predetermined pitch λ (FIG. 1(b)). The first attachment members 41 are fixed on the surface, which is on the reverse side of the drawing sheet of FIG. 1(a) (the surface to be the inner-surface side of the belts of a produced diaper).

Then, as shown in FIG. 1(b), while the strip-shaped web W is carried along, the web W is cut along a wave-shaped cut-off line L that is continuous in the longitudinal direction of the web W. This produces comb-shaped first and second separate webs W1 and W2. The first separate web W1 includes a plurality of first tapered portion 13, which are connected together along a first lateral portion S1 that includes one side edge of the web W. The second separate web W2 includes a plurality of second tapered portions 23, which are connected together along a second lateral portion S2 that includes the other side edge of the web W. The first and second tapered portions 13 and 23 each have a tapered shape with the width thereof gradually decreasing away from the first and second lateral portions S1 and S2 toward the free end portions 12 and 22, respectively. The first and second lateral portions S1 and S2 are to be the fixed end portions 11 and 21 of the first and second belts (FIG. 4(a)) after the step of cutting the lateral portions S1 and S2 to be described later.

The web W is cut so that the first attachment member 41 is included in each first tapered portion 13. Moreover, the wavelength of the cut-off line L along which the web W is cut is equal to the pitch λ of the first attachment members 41.

Figure 1C:
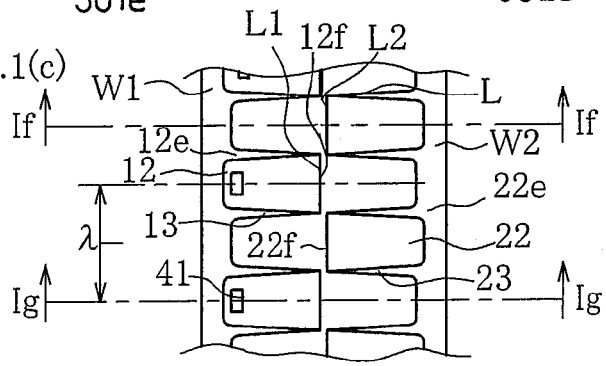

Then, the two separate webs W1 and W2 are carried while being separated from each other in the vertical direction, for example. Then, the first tapered portion 13 is folded back at a folded portion 12f along a first folding line L1 of the free end portion 12 so that the free end portion 12 of the first tapered portion 13 is laid on a base portion 12e of the first tapered portion 13 that is closer to the first side edge portion S1, as shown in FIG. 1(c). The first folding line L1 is a line that extends in a direction perpendicular to the longitudinal direction generally at the center of the first tapered portion 13 with respect to the longitudinal direction. FIG. 1(g) is a cross-sectional view taken along line Ig-Ig in FIG. 1(c). In this folding process, the free end portion 12 of the first tapered portion 13 is laid on and temporarily attached to the base portion 12e via an adhesive 9A such as a hot-melt resin, as shown in FIG. 1(g) (the first temporary attachment).

The second tapered portion 23 is folded back at a folded portion 22f along a second folding line L2 of the free end portion 22 so that the free end portion 22 of the second tapered portion 23 is laid on a base portion 22e of the second tapered portion 23 that is closer to the second lateral portion S2, as shown in FIG. 1(c). The second folding line L2 is a line that extends in a direction perpendicular to the longitudinal direction generally at the center of the second tapered portion 23 with respect to the longitudinal direction. FIG. 1(f) is a cross-sectional view taken along line If-If in FIG. 1(c). In this folding process, the free end portion 22 of the second tapered portion 23 is laid on and temporarily attached to the base portion 22e via the adhesive 9A such as a hot-melt resin, as shown in FIG. 1(f) (the first temporary attachment).

Figure 1D:
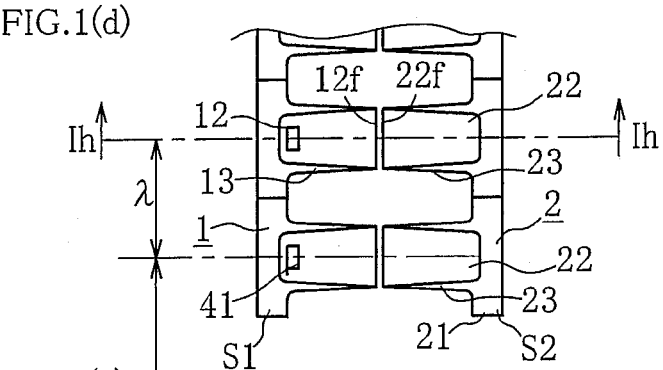

When the webs are carried while being separated from each other as described above, the phases of the first separate web W1 and the second separate web W2 are shifted from each other in the carrying direction Y of the web W so that the folded portion 12f of the first tapered portion 13 and the folded portion 22f of the second tapered portion 23 will later come closer to each other as shown in FIG. 1(d). Specifically, the positional relationship between the separate webs W1 and W2 is changed so that the folded portions 12f and 22f thereof face each other. The change of the positional relationship may be achieved by shifting either web W1 (W2) from the other. For example, the first tapered portion 13 and the second tapered portion 23 can be made to face each other by delaying one of the first and second separate webs W1 and W2 by ($\lambda/2+n\lambda$).

Then, the first and second separate webs W1 and W2 are cut simultaneously in the lateral portions S1 and S2 so that each set of pieces include the first and second tapered portions 13 and 23, which have come closer to each other through the change of the positional relationship, thus producing a pair of the first and second belts 1 and 2. The cut-off line in this cutting process is a line that extends in the width direction X of the first and second separate webs W1 and W2.

Figure 1E:
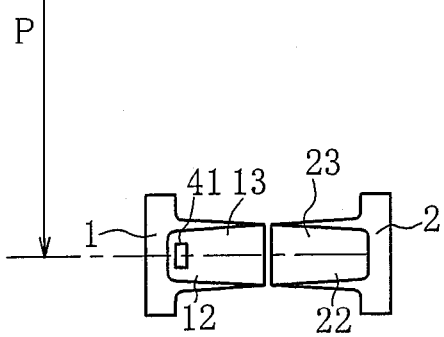
Figure 1F:
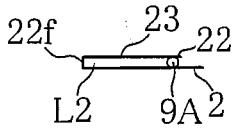
Figure 1G:
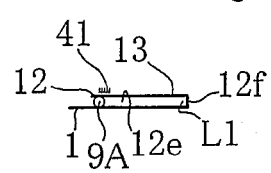
Figure 1H:
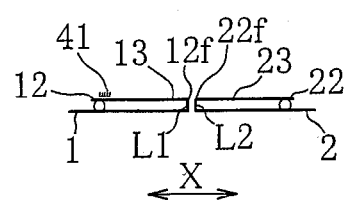

FIG. 1(h) is a cross-sectional view taken along line Ih-Ih in FIG. 1(d). As shown in FIG. 1(h), the first belt 1 and the second belt 2 are carried symmetrically about the center in the width direction X generally perpendicular to the carrying direction Y.

After pairs of the first and second belts 1 and 2 are produced, the interval between adjacent pairs of the belts 1 and 2 are increased to a predetermined interval P, as shown in FIG. 1(e). Thus, the pitch P of the pairs of belts becomes equal to the pitch P or the total length of a diaper to be produced later.

Then, the pairs of the first and second belts 1 and 2 are placed on a continuous piece 30 at a predetermined pitch P in the carrying direction Y, as shown in FIG. 2(a). The continuous piece 30 is a carrier web being a single sheet of web or a laminate of a plurality of sheets of web, for example, and is later cut to form the diaper main body 3. The continuous piece 30 is formed so that portions thereof to be the back portions 3b and portions thereof to be the front portions 3f alternate with each other in the longitudinal direction. Each pair of the first and second belts 1 and 2 is placed so as to be laid on a portion of the continuous piece 30 that is to be the back portion 3b (FIG. 3(b)), and is temporarily attached to that portion via an adhesive 9B such as a hot-melt resin as shown in FIG. 2(d) (the second temporary attachment). With the second temporary attachment, each pair of the first and second belts 1 and 2 can be carried so that it will not come off the continuous piece 30.

In the placement step, the first belt 1 is placed so that the fixed end portion 11 of the first belt 1 (a portion of the first lateral portion S1) protrudes from a first side edge 301e of the continuous piece 30. The second belt 2 is placed so that a fixed end portion 21 of the second belt 2 (a portion of the second lateral portion S2) protrudes from a second side edge 302e opposite to the first side edge 301e. The belts 1 and 2 are placed so that the tips of the folded tapered portions 13 and 23 are positioned at (coincide with) the side edges 301e and 302e, respectively.

After the second temporary attachment, the fixed end portions 11 and 21 protruding from the side edges 301e and 302e of the continuous piece 30 are folded back as shown in FIG. 2(b). Thus, the continuous piece 30 is sandwiched between the fixed end portions 11 and 21 and the tapered portions 13 and 23. Then, the folded portions of the fixed end portions 11 and 21 are at least partially fixed to portions of the continuous piece 30 in the vicinity of the side edges 301e and 302e, respectively.

Figure 3A:
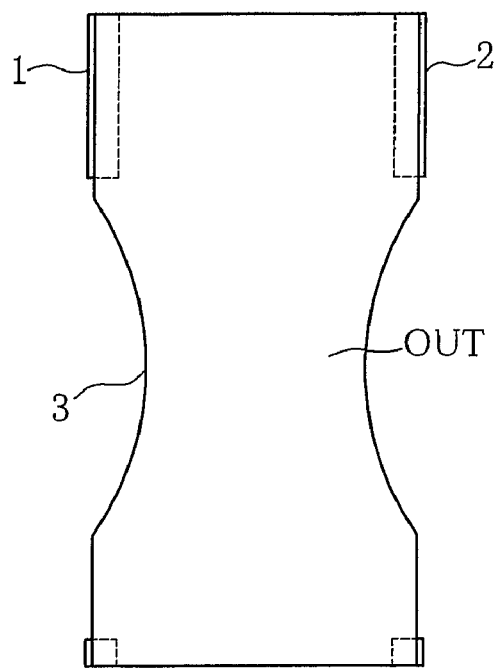
FIGS. 3(a), 3(b) and 3(c) are a back side view, a front view and a cross-sectional view taken along line IIIc-IIIc, respectively, of a produced diaper.
Figure 3B:
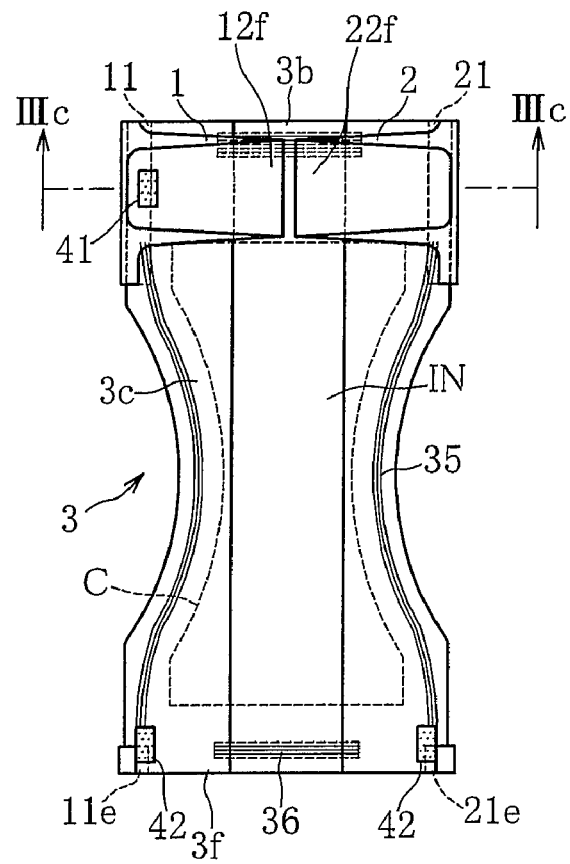

Specifically, the fixed end portions 11 and 21 of the belts 1 and 2 are fixed to opposite end portions of the back portion 3b (FIG. 3(b)) in the around-the-torso direction.

Figure 3C:
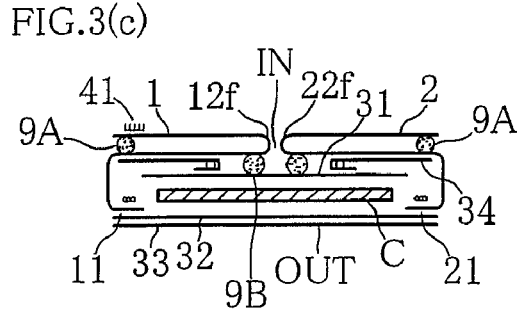
Figure 3D:
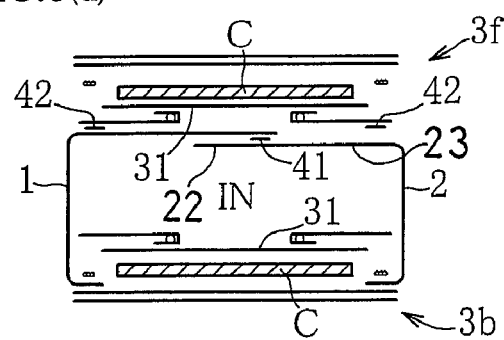
FIG. 3(d) is a schematic cross-sectional view of a diaper when worn.
Figure 7A:
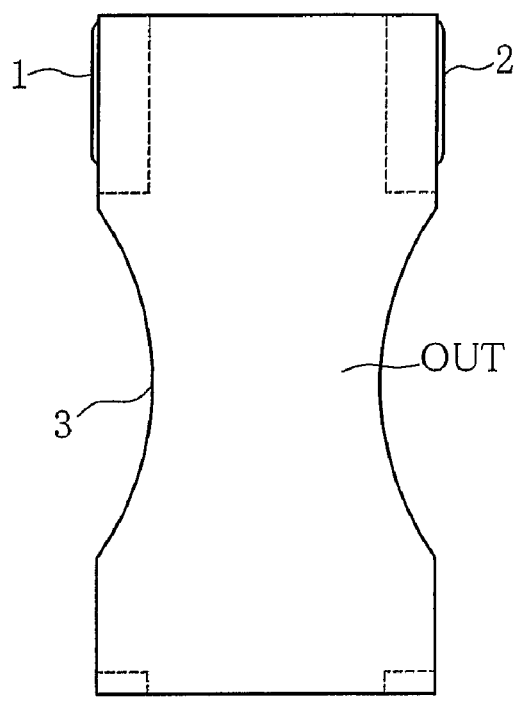
FIGS. 7(a) and 7(b) are a back side and a front view, respectively, showing a produced diaper.
Figure 7B:
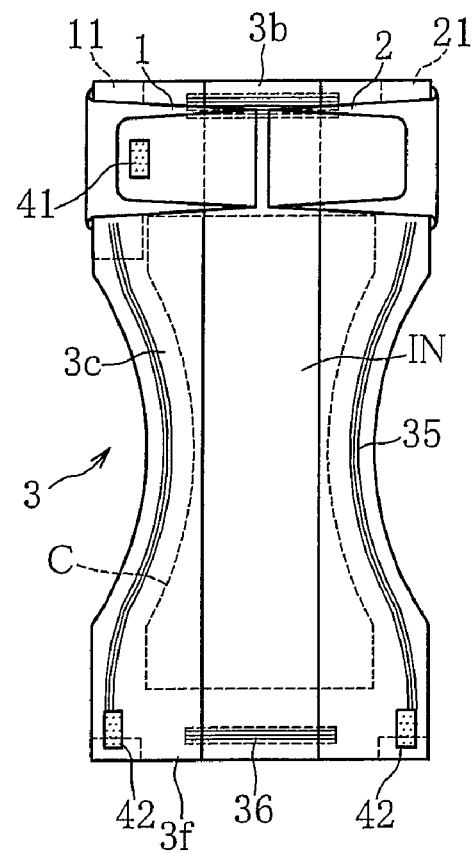

After the belts 1 and 2 are fixed, the absorbent body C, the back sheet 32, the outer sheet 33 (FIG. 3(c)), etc., are layered on the continuous piece 30, as shown in FIG. 2(c), thereby producing a laminate being the diaper main body 3 (FIG. 3(b)). Then, the laminate including the continuous piece 30 is severed at a predetermined pitch P into individual diapers. In other words, the laminate is cut along cut-off lines extending in the width direction of the laminate so as to produce diapers each having a length of P in the longitudinal direction of the diaper main body. In this cutting process, the fixed end portions 11 and 21 of the belts 1 and 2 may be cut so that the tapered portions 13 and 23 are not cut; In such a case, torn pieces 11e and 21e (FIG. 3(b)) of the fixed end portions 11 and 21 will be left on the front portion 3f. Alternatively, the cutting may be done so that only the continuous piece 30 is cut at a position such that the fixed end portions 11 and 21 of the belts 1 and 2 are not cut.

In the step of cutting the continuous piece 30, a portion of the continuous piece 30 that forms the crotch portion 3c may be partially removed (trimmed). The trimming may be done before or after the step of cutting the continuous piece 30.

This produces a diaper as shown in FIGS. 3(b) and 3(c). As shown in these figures, in the produced diaper, the first and second belts 1 and 2 folded respectively at the folded portions 12f and 22f are folded so as to be laid on the inner-surface side IN of the back portion 3b.

The fixed end portion 11 of the first belt 1 shown in FIG. 3(b) is folded back at one end of the back portion 3b in the around-the-torso direction and fixed to the back portion 3b. The fixed end portion 21 of the second belt 2 is folded back at the other end of the back portion 3b in the around-the-torso direction and fixed to the back portion 3b. During shipping of the diapers, the diaper main body 3 may be folded in two in the crotch portion 3c and the front portion 3f may be temporarily attached on the first belt 1 and the second belt 2 by means of the second attachment member 42. The front portion 3f may be temporarily attached on either belt 1 (2).

When the back sheet 32 is layered on the continuous piece 30, the fixed end portions 11 and 21 of the belts 1 and 2 may be bonded to both the anti-leak walls 34 and the back sheet 32 while being sandwiched between the anti-leak walls 34 and the back sheet 32 shown in FIG. 4(b). Then, the belts 1 and 2 are more strongly fixed to the diaper main body 3.

Next, how the present diaper is worn will be described.

The wearer opens the first belt 1 and the second belt 2 folded as shown in FIGS. 3(b) and 3(c), disengaging the first and second temporary attachments. The wearer in a stand-up position attaches the tip portions of the belts 1 and 2 to each other on the abdominal side of the wearer by means of the first attachment member 41 as shown in FIG. 3(d). After the attachment, the wearer attaches the front portion 3f to the first and second belts 1 and 2, which have been attached to each other, via the second attachment members 42 and 42, thus wearing the diaper. The front portion 3f may be attached to one of the belts 1 and 2 via the second attachment members 42 and 42.

Second Embodiment

FIGS. 5(a) to 8(c) each show a second embodiment.

In a diaper produced in the second embodiment, the fixed end portions 11 and 21 of an increased width of the first and second belts 1 and 2 are generally entirely folded back and fixed to the diaper main body 3, as clearly shown in FIGS. 7(a), 7(b) and 8(a) to 8(c).

A diaper whose belts are fixed in such a manner has a desirable appearance because the fixed end portions 11 and 21 of an increased width do not protrude from the diaper main body 3, and the belts 1 and 2 are more strongly fixed to the diaper main body 3 because the area of attachment between the belts 1 and 2 and the diaper main body 3 is increased.

Next, an example of a method for producing a diaper of the present embodiment will be described.

In this example, the first separate web W1 and the second separate web W2 are spaced apart from each other after the web W is cut as shown in FIG. 5(b) and before the free end portion 12 of the first tapered portion 13 and the free end portion 22 of the second tapered portion 23 are folded. Specifically, the first separate web W1 and the second separate web W2 are spaced apart from each other so that the second lateral portion S2 and the first lateral portion S1 move away from each other in the width direction X of the web as shown in FIG. 5(c). In this spacing process, only one separate web W1 (W2) may be moved in the width direction X of the web or both of the two separate webs W1 and W2 may be moved in the width direction X of the web.

Then, the phases of the first and second belts 1 and 2 are shifted in the carrying direction Y of the web W so that the folded portions 12f and 22f of the belts 1 and 2 come closer to each other as shown in FIG. 5(d). Specifically, the positional relationship between the belts 1 and 2 is changed so that the folded portions 12f and 22f face each other. The phase of one belt 1 (2) may be shifted.

Through the spacing process, each pair of the first and second belts 1 and 2 is placed so that the first and second lateral portions S1 and S2 to be the fixed end portions 11 and 21 of the first and second belts 1 and 2 are generally entirely protruding from the side edges 301e and 302e, respectively, of the continuous piece 30 as shown in FIG. 6(a). In the present embodiment, the tips of the tapered portions 13 and 23 are placed on the inner side with respect to the side edges 301e and 302e, respectively.

After the placement process, the fixed end portions 11 and 21 protruding from the side edges 301e and 302e, respectively, of the continuous piece 30 are folded back as shown in FIG. 6(b). Then, the folded portions of the fixed end portions 11 and 21 are at least partially fixed to portions of the continuous piece 30 in the vicinity of the side edges 301e and 302e, respectively.

The other production steps are similar to those of the first embodiment, for which like members are denoted by like reference numerals and will not be further described below.

As shown in FIGS. 9(a) to 9(i) and 10(a) to 10(d), the first belt 1 and the second belt 2, having the tapered portions 13 and 23 folded, may be temporarily attached to each other in advance to form a single temporarily-attached web, in which case the first and second belts 1 and 2 can be handled as a single web in subsequent steps.

The first tapered portion 13 of the first belt 1 is folded at the folded portion 12f along the first folding line L1 as shown in FIG. 9(a). Then, the second belt 2 is placed so that the free end portion of the second belt 2 is laid on the first belt 1. Then, the folded portion 12f of the first belt 1 and an intermediate portion of the second tapered portion 23 of the second belt 2 (the portion to be the folded portion 22f) are temporarily attached to each other via an adhesive 9C such as a hot-melt.

After the temporary attachment process, the second tapered portion 23 of the second belt 2 is folded at the folded portion 22f along the second folding line L2 as shown in FIG. 9(b) to form a single temporarily-attached web. Then, the belts 1 and 2 are temporarily attached to the continuous piece 30 as shown in FIG. 9(c), after which the fixed end portions 11 and 21 of the belts 1 and 2 are fixed to the continuous piece 30 as shown in FIG. 9(d).

With the method shown in FIGS. 9(e) to 9(h), the folding is done on the continuous piece 30.

Specifically, first, the tapered portion 13 of the first belt 1 placed on the continuous piece 30 is folded at the folded portion 12f along the first folding line L1 as shown in FIG. 9(e).

Then, the second belt 2 is placed on the continuous piece 30 so that the free end portion of the second belt 2 is laid on the first belt 1 as shown in FIG. 9(f). Then, the folded portion 12f of the first belt 1 and an intermediate portion of the second tapered portion 23 of the second belt 2 (the portion to be the folded portion 22f) are temporarily attached to each other.

Then, the second tapered portion 23 of the second belt 2 is folded at the folded portion 22f along the second folding line L2 as shown in FIG. 9(g). Then, the fixed end portions 11 and 21 of the belts 1 and 2 are fixed to the continuous piece 30 as shown in FIG. 9(h).

It is preferred that the bonding margins of the folded portions 12f and 22f of the belts 1 and 2 are large in the thickness direction of the web as shown in FIG. 9(i).

The belts 1 and 2 may be temporarily attached to each other while being shifted from each other in the vertical direction as shown in FIGS. 10(a) to 10(d).

Figure 10A:
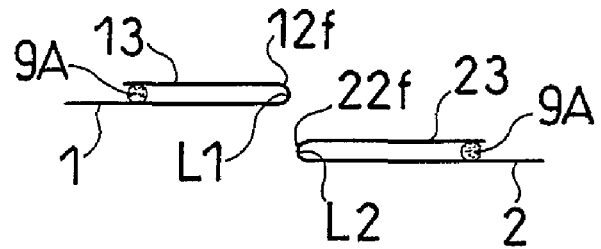
FIGS. 10(a) to 10(d) are schematic cross-sectional views showing a variation of the present invention.
Figure 10B:
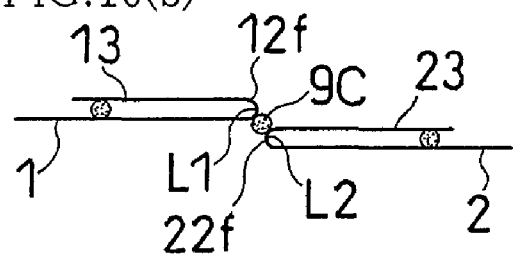

The first belt 1 and the second belt 2 folded at the folded portions 12f and 22f, respectively, are placed while being positionally shifted from each other in the vertical direction as shown in FIG. 10(a). Then, the folded portions 12f and 22f are temporarily attached to each other as shown in FIG. 10(b) to form a single temporarily-attached web. The folded portions 12f and 22f may or may not be placed so that the folded portions 12f and 22f are laid on each other in the vertical direction.

Figure 10C:
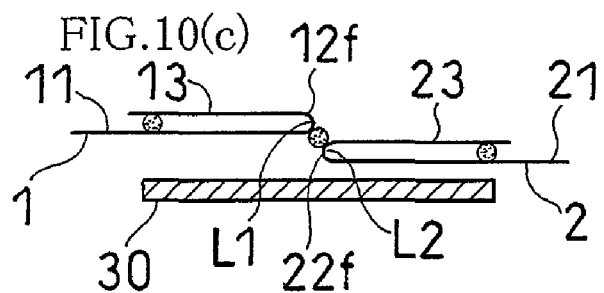
Figure 10D:
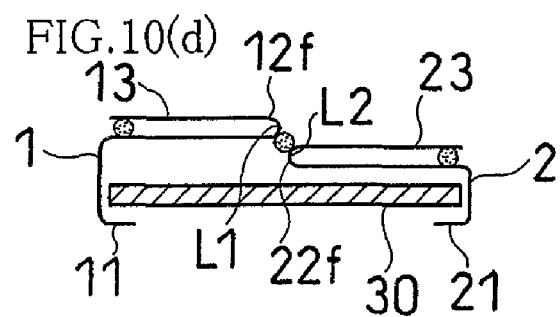

Then, the temporarily-attached webs 1 and 2 are placed on the continuous piece 30 as shown in FIG. 10(c). After the placement process, the fixed end portions 11 and 21 are fixed to the continuous piece 30.

Embodiment 3

FIGS. 11 to 14 each show the third embodiment.

FIGS. 13(a) to 13(d) and 14(a) to 14(c) each show a diaper of the third embodiment.

Figure 13A:
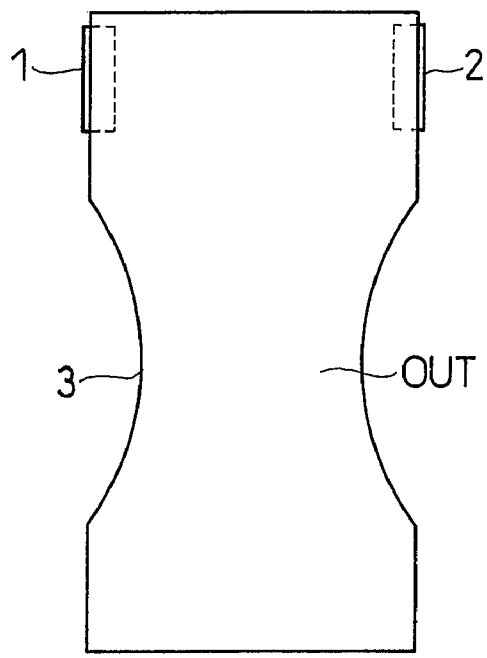
Figure 13B:
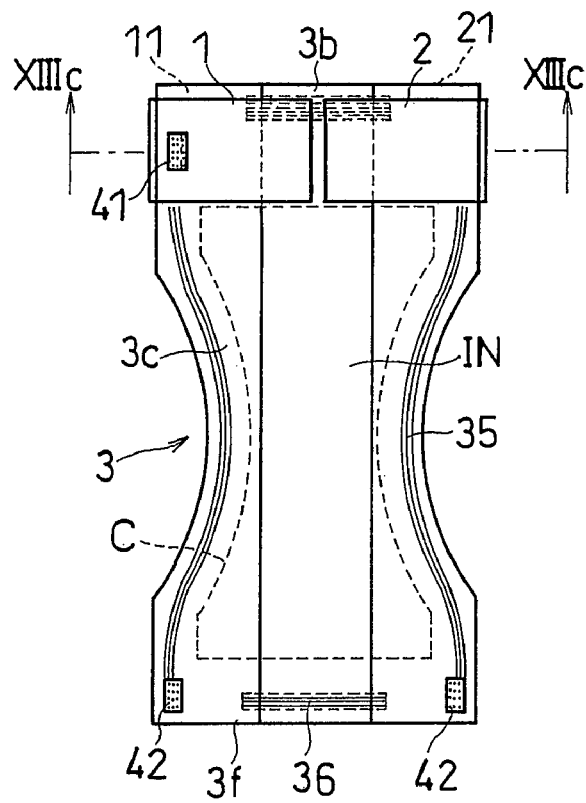
Figure 13C:
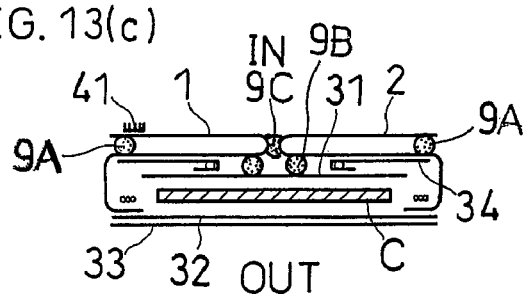
Figure 13D:
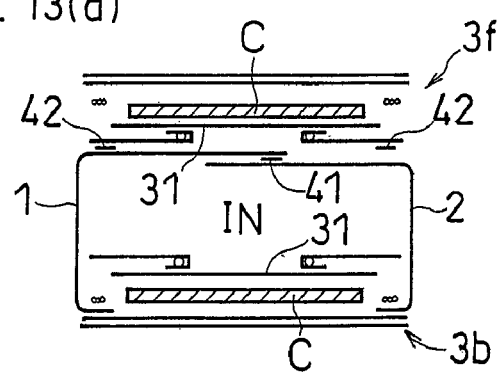
FIG. 13(d) is a schematic cross-sectional view of a diaper when worn.
Figure 14A:
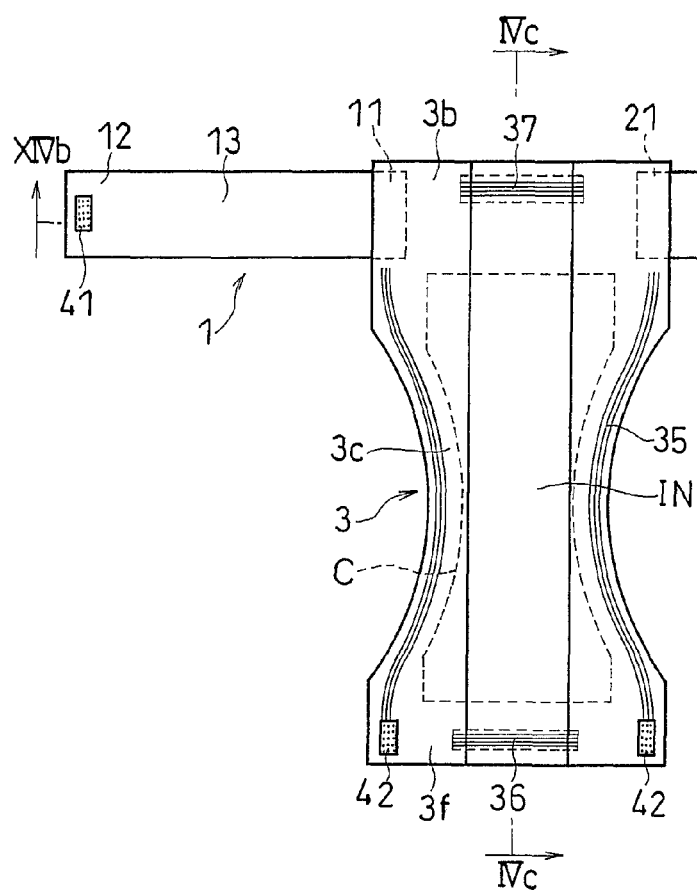
FIGS. 14(a), 14(b) and 14(c) are a front view and cross-sectional views taken along lines XIVb-XIVb and XIVc-XIVc, respectively, showing a diaper with belts being spread out.
Figure 14C:
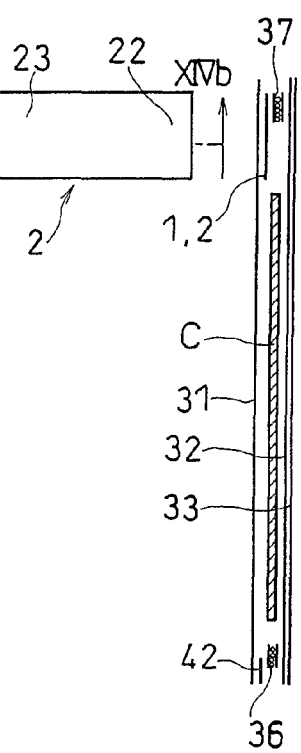
Figure 14B:
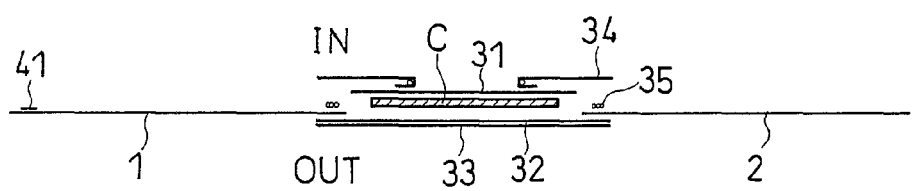

The belts 1 and 2 of the present embodiment have a constant width from the fixed end portions 11 and 21 to the free end portions 12 and 22 as shown in FIGS. 13(b) and 14(a).

Otherwise, the structure of the diaper of the present embodiment is similar to that of the first embodiment, and will not be further described below.

Figure 11A:
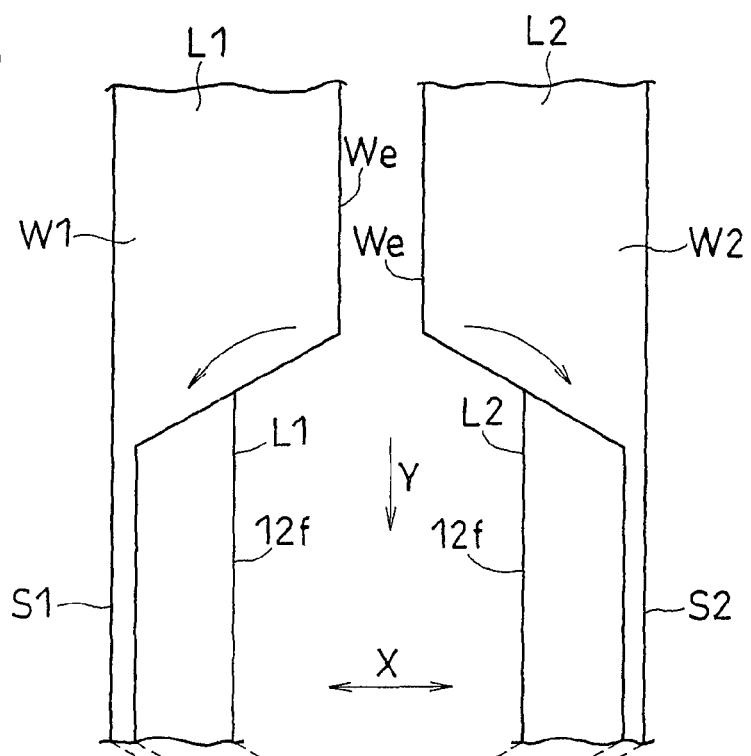
FIGS. 11(a) to 11(c) are front views and FIG. 11(d) is a cross-sectional view taken along line XId-XId, showing an example of a method for producing belts according to the present invention.

In the third embodiment, two webs W1 and W2 to be the first and second belts 1 and 2 are used as shown in FIG. 11(a). The first web W1 and the second web W2 are each continuous in the carrying direction Y, and are processed while being carried in the carrying direction Y in parallel to each other. The webs W1 and W2 have generally the same width.

The first web W1 and the second web W2 are folded back by means of a sailor (a folding apparatus) (not shown). The first web W1 is folded back along the first folding line L1, which is continuous in the longitudinal direction Y of the first web W1. Similarly, the second web W2 is folded back along the second folding line L2, which is continuous in the longitudinal direction Y of the second web W2.

The inner end portions We of the webs W1 and W2, being close to each other, are folded back toward the lateral portions S1 and S2, respectively, opposing the inner end portions We. The first web W1 is folded back so that the first lateral portion S1 and other portions of the first web W1 are not laid on each other (so that the inner end portion We is not laid on the first lateral portion S1). In order to maintain the folded position, the first web W1 is temporarily attached via the adhesive 9A as shown in FIG. 11(d). The second web W2 of FIG. 11(a) is folded back so that the second lateral portion S2 and other portions of the second web W2 are not laid on each other (so that the inner end portion We is not laid on the second lateral portion S2). In order to maintain the folded position, the second web W2 is temporarily attached via the adhesive 9A as shown in FIG. 11(d).

Figure 11B:
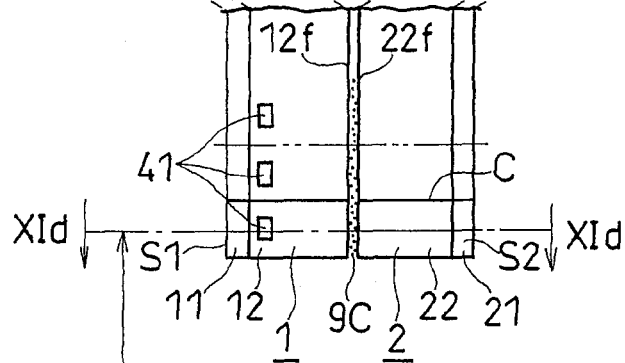

Then, the carrying paths of the webs W1 and W2 are changed so that the first folding line L1 and the second folding line L2 come closer to each other as shown in FIG. 11(b). Alternatively, the carrying path of one web W1 (W2) may be changed.

After the carrying path is changed, the folded portion 12f of the first folding line L1 and the folded portion 22f of the second folding line L2 are temporarily attached to each other via the adhesive 9C to form a single temporarily-attached web. FIG. 11(d) is a cross-sectional view taken along line XId-XId in FIG. 11(b). The belts 1 and 2 are carried as a single web, in which the folded portions 12f and 22f are temporarily attached to each other, as shown in FIG. 11(d). The temporarily-attached web is formed so that the first belt 1 and the second belt 2 are symmetric about the center in the width direction X generally perpendicular to the carrying direction Y. The first attachment member 41 is fixed to the first web W1.

Then, the first web W1 and the second web W2 are cut along the cut-off line C extending the width direction X of these webs to thereby form pairs of the first and second belts 1 and 2.

Figure 11C:
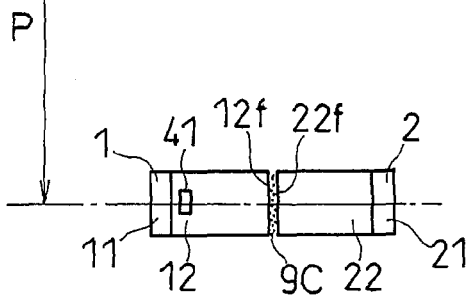
Figure 11D:
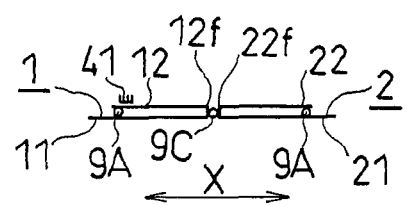

After the cutting process, the interval between adjacent pairs of the belts 1 and 2 in the carrying direction Y is increased to a predetermined pitch P as shown in FIG. 11(c). Thus, the pitch P of the pairs of belts becomes equal to the pitch P of diapers to be produced or the entire length of a produced diaper.

Then, pairs of the first and second belts 1 and 2 are placed at a predetermined pitch P in the carrying direction Y of the continuous piece 30 as shown in FIG. 12(a). Pairs of the first and second belts 1 and 2 are placed at a predetermined pitch in the carrying direction Y of the continuous piece 30 so as to be laid on a portion to be the back portion (FIG. 13(b)) of the continuous piece 30 forming the diaper main body 3.

Each pair of the first and second belts 1 and 2 is placed so as to be laid on the back portion 3b (FIG. 13(b)) of the continuous piece 30 and is temporarily attached to that portion.

FIG. 12(d) is a cross-sectional view taken along line XIId-XIId in FIG. 12(a). In the placement step, the belts 1 and 2 are placed so that the fixed end portions 11 and 21 of the first and second belts 1 and 2 are protruding from the first and second side edges 301e and 302e of the continuous piece 30 as shown in FIG. 12(d).

After the temporary attachment process, the fixed end portions 11 and 21 protruding from the side edges 301e and 302e, respectively, of the continuous piece 30 are folded back as shown in FIG. 12(b). FIG. 12(e) is a cross-sectional view taken along line XIIe-XIIe in FIG. 12(b). As shown in FIG. 12(e), the fixed end portions 11 and 21 are folded back along the side edges 301e and 302e, respectively, of the continuous piece 30, and the folded portions of the fixed end portions 11 and 21 are at least partially fixed to portions of the continuous piece 30 in the vicinity of the side edges 301e and 302e, respectively.

Thus, the fixed end portions 11 and 21 are fixed to portions of the continuous piece 30 that are to be the opposing end portions of the back portion 3b in the around-the-torso direction.

Then, the continuous piece 30 is severed at a predetermined pitch P into individual diapers as shown in FIG. 13(b). This cutting is done in a portion where the belts 1 and 2 are not placed.

In the present invention, in a case where the carrying paths of both of the webs W1 and W2 are changed after folding back both of the first and second webs W1 and W2, the carrying path of the first web W1 and/or that of the second web W2 are changed so that the first folding line L1 and the second folding line L2 come close to each other or coincide with each other. In a case where the carrying path of the first web W1 and/or that of the second web W2 are changed after one web W1 (W2) is folded back (FIG. 9), the carrying paths of the webs W1 and W2 are changed so that one folding line L1 (L2) and the other folding line L2 (L1) come close to each other or coincide with each other. In a case where both of the webs W1 and W2 are folded back after the carrying paths are changed so that the webs W1 and W2 are laid on each other, the carrying path of the first web W1 and/or that of the second web W2 are changed so that portions of the webs to be the folding lines L1 and L2 come close to each other or coincide with each other.

Figures 8A, 8B, 8C:
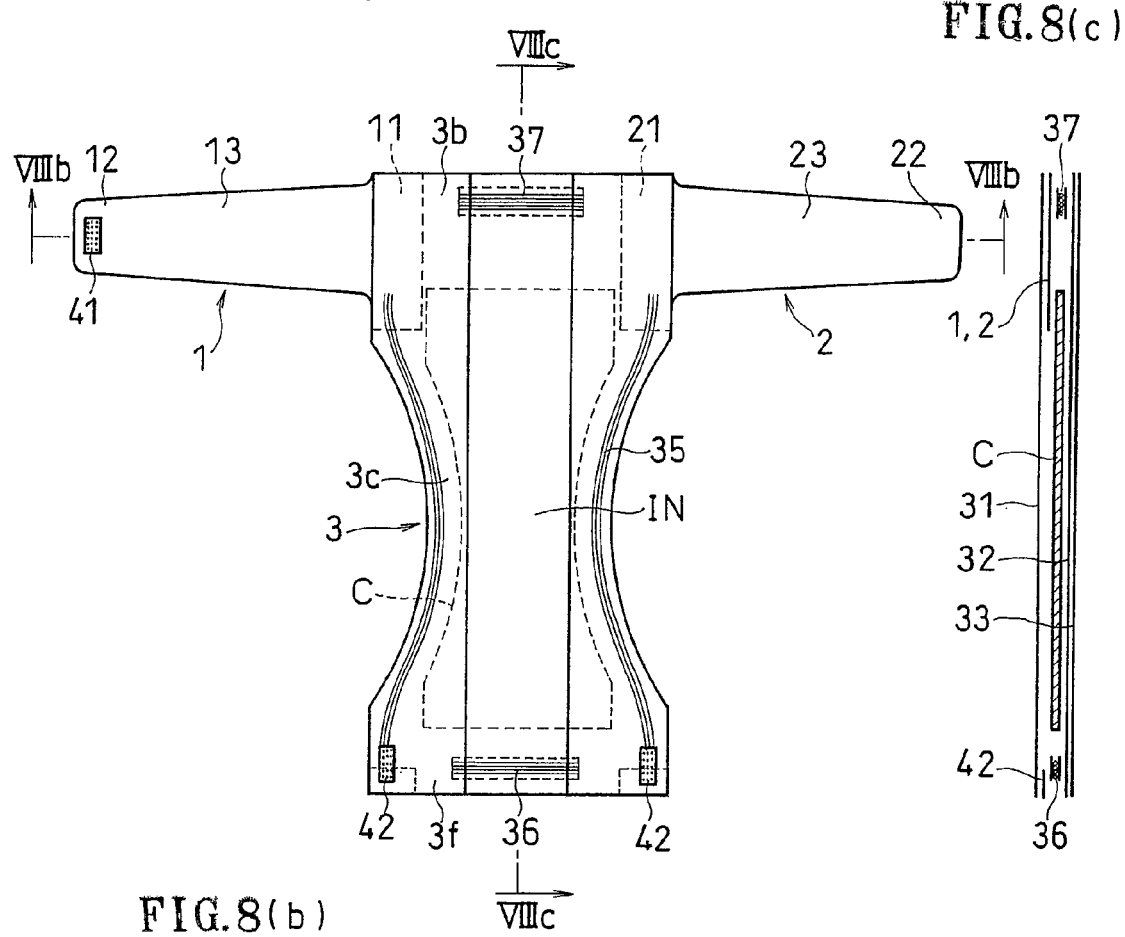
FIGS. 8(a), 8(b) and 8(c) are a front view and cross-sectional views taken along lines VIIIb-VIIIb and VIIIc-VIIIc, respectively, showing a diaper with belts being spread out.

While the first and second belts 1 and 2 of FIG. 4(b) are attached to the anti-leak walls 34 of the top sheet 31 in the embodiments above, the first and second belts 1 and 2 may be attached to the top sheet 31 itself or to both of the top sheet 31 and the anti-leak walls 34 as shown in FIG. 8(b).

As the continuous piece 30 of FIG. 2(a), the back sheet 32 and the outer sheet 33 of FIG. 4(b) may be employed, wherein the first and second belts 1 and 2 may be fixed on the inner-surface side or the outer-surface side of the back sheet 32 or the outer sheet 33. Only one of the back sheet 32 and the outer sheet 33 may be employed as the continuous piece 30.

While the first and second belts 1 and 2 of FIG. 3(c) are placed on the inner-surface side of the diaper in the embodiments above, the first and second belts 1 and 2 may be placed on the outer-surface side. In such a case, the end portions of the first and second belts 1 and 2 are folded back on the inner-surface side of the diaper.

The folding back of the belts 1 and 2 may be done by folding back the first and second lateral portions S1 and S2 of the first and second separate webs W1 and W2 of FIG. 1(b) after cutting the web W.

Moreover, while the fixed end portions 11 and 21 of the first and second belts 1 and 2 are folded back in the embodiments above, the fixed end portions 11 and 21 of the first and second belts 1 and 2 may fall within the width of the continuous piece 30 so that the fixed end portions 11 and 21 of the first and second belts 1 and 2 can be fixed to the continuous piece 30 without being folded back. This is also included within the scope of the present invention. Moreover, the opposing lateral portions of the continuous piece 30 may be folded back without folding back the fixed end portions 11 and 21 of the first and second belts 1 and 2, wherein the fixed end portions 11 and 21 of the belts 1 and 2 may be fixed to the folded portions.

While preferred embodiments of the present invention have been described above with reference to the drawings, various changes and modifications thereto are readily obvious to those skilled in the art reading the present embodiment.

For example, the first attachment member 41 may be provided on the outer-surface side of the second belt 2.

Moreover, the temporary attachment may be realized through welding by means of a touch fastener or an ultrasonic means, instead of using a hot-melt resin.

In a case where the diaper is used as an incontinence pad, the absorbent body C may be made smaller.

The present diaper may have such a structure that allows alternative usage, in stead of the usage (how the diaper is worn) as shown in FIG. 3(*d*).

Therefore, such changes and modifications are deemed to fall within the scope of the present invention, which is defined by the appended claims.

INDUSTRIAL APPLICABILITY

The present invention can be applied to the production of diapers.

The invention claimed is:

1. A method for producing a diaper, the diaper comprising: a diaper main body including a front portion covering an abdominal side of a wearer, a back portion covering a back side of the wearer, and a crotch portion between the front portion and the back portion; a first belt including a first end portion fixed to one end portion of the back portion in an around-the-torso direction; and a second belt including a second end portion fixed to the other end portion of the back portion in the around-the-torso direction, wherein the first and second belts are attached to each other when wearing the diaper to thereby fasten the diaper around the torso of the wearer, the method comprising the steps of:

carrying a strip-shaped first web being continuous in a carrying direction and including a first lateral portion to be the first end portion;

folding back the first web along a first folding line that is continuous in a longitudinal direction of the first web while carrying the first web;

carrying a strip-shaped second web being continuous in a carrying direction and including a second lateral portion to be the second end portion;

folding back the second web along a second folding line that is continuous in a longitudinal direction of the second web while carrying the second web;

changing a carrying path of the first web and/or that of the second web so that the first folding line and the second folding line come close to each other or coincide with each other;

successively forming pairs of the first and second belts by cutting the first web and the second web along cut-off lines extending in the width direction of the webs after the step of folding back the first and second webs and the step of changing the carrying path;

placing pairs of the first and second belts at a predetermined interval in a carrying direction of a continuous piece forming the diaper main body so that each pair is laid on a portion of the continuous piece to be the back portion;

temporarily attaching the first and second belts, which have been placed at the predetermined interval, to the portion of the continuous piece to be the back portion;

fixing each pair of the first and second belts to the continuous piece by fixing the first lateral portion of the first belt to a portion of the continuous piece to be one end portion of the back portion in the around-the-torso direction and fixing the second lateral portion of the second belt to a portion of the continuous piece to be the other end portion of the back portion in the around-the-torso direction; and severing the continuous piece with the first and second belts fixed thereon at the predetermined interval into individual diapers, the method further comprising, after the step of changing the carrying path and before the step of cutting the first and second webs, a step of temporarily attaching a portion of the first web along the first folding line and a portion of the second web along the second folding line to each other to form a single temporarily-attached web.

* * * * *